United States Patent [19]
Chin et al.

[11] Patent Number: 5,269,789
[45] Date of Patent: Dec. 14, 1993

[54] MULTIPLE LIGATING BAND DISPENSER FOR LIGATING INSTRUMENTS

[75] Inventors: Yem Chin, Burlington; Michael S. H. Chu, Brookline, both of Mass.

[73] Assignee: Boston Scientific Corporation, Watertown, Mass.

[21] Appl. No.: 960,081

[22] Filed: Oct. 9, 1992

[51] Int. Cl.⁵ .................................. A61B 17/12
[52] U.S. Cl. ............................................ 606/140
[58] Field of Search ................. 606/139, 140, 144

[56] References Cited

U.S. PATENT DOCUMENTS

| | | | |
|---|---|---|---|
| 3,155,094 | 11/1964 | Hamilton | 606/140 |
| 3,382,273 | 6/1965 | Banich et al. | |
| 3,687,138 | 8/1972 | Jarvik | |
| 3,760,810 | 9/1973 | Van Hoorn | |
| 3,834,392 | 9/1974 | Lampman et al. | |
| 3,870,048 | 3/1975 | Yoon | |
| 3,911,923 | 10/1975 | Yoon | |
| 3,934,589 | 1/1976 | Zimmer | |
| 3,958,576 | 5/1976 | Komiya | |
| 3,967,625 | 7/1976 | Yoon | |
| 3,989,049 | 11/1976 | Yoon | |
| 4,103,680 | 8/1978 | Yoon | 128/6 |
| 4,226,239 | 10/1980 | Polk et al. | |
| 4,230,116 | 10/1980 | Watson | |
| 4,257,419 | 3/1981 | Goltner et al. | |
| 4,257,420 | 3/1981 | Terayama | |
| 4,267,839 | 5/1981 | Laufe et al. | |
| 4,374,523 | 2/1983 | Yoon | |
| 4,471,766 | 9/1984 | Terayama | 128/6 |
| 4,548,201 | 10/1985 | Yoon | |
| 4,735,194 | 4/1988 | Stiegmann | 128/6 |
| 4,794,927 | 1/1989 | Yoon | |
| 4,990,152 | 2/1991 | Yoon | |
| 5,026,379 | 6/1991 | Yoon | 606/141 |
| 5,122,149 | 6/1992 | Broome | 606/140 |
| 5,203,863 | 4/1993 | Biddia | 606/140 |

Primary Examiner—Stephen C. Pellegrino
Assistant Examiner—Tamara L. Graysay
Attorney, Agent, or Firm—Pearson & Pearson

[57] ABSTRACT

A ligating band dispenser for dispensing a plurality of ligating bands individually during a sequence of operations for a ligating instrument. Interfitted housing and piston segments support a plurality of ligating bands at axially spaced locations. Retraction of the piston segment dispenses on ligating band and shifts the remaining ligating bands distally and axially. After retraction, the piston is biased forward so a next retraction dispenses another ligating band.

29 Claims, 5 Drawing Sheets

MULTIPLE LIGATING BAND DISPENSER FOR LIGATING INSTRUMENTS

BACKGROUND OF THE INVENTION

1. Field of the Invention

This invention generally relates to ligating instruments and more particularly to instruments capable of dispensing ligating bands in a sequential manner.

2. Description of Related Art

The treatment of various types of lesions including internal hemorrhoids by ligation is well known. The object of ligation is to position an elastic cord, or ligating band, at the lesion to stop circulation through tissue and allow the tissue to die whereupon the body sloughs off the dead tissue.

The following United States Letters Patent disclose various embodiments of ligating instruments:

3,760,810 (1973) Van Hoorn
4,257,419 (1981) Göltner et al
4,735,194 (1988) Stiegmann U.S. Pat. No. 3,760,810 to Van Hoorn discloses an instrument for facilitating the placement of a single ligating band or set of bands. The instrument includes, at its distal end, a ligating band dispenser comprising two rigid, concentric tubes. The tubes can slide with respect to each other under the control of a trigger mechanism at the proximal end of the instrument. A rigid endoscope having internal passages forming a suction path and a light path interconnect the trigger mechanism and dispenser. The inner tube can be loaded with a set of one or more elastic rings or ligating bands. A separate stopper bar attaches to the instrument to prevent premature dispensing. When the instrument is located proximate a lesion, a surgeon removes the stopper bar and applies vacuum to draw tissue into a hollow passage at the distal end of the instrument. Pulling on the trigger retracts the inner tube. A radial surface or shoulder on the outer tube engages the ligating band so it can not displace with the inner tube. As the inner tube is withdrawn from the ligating band, it collapses onto the tissue U.S. Pat. No. 4,257,419 to Goltner et al discloses a rigid endoscope that includes a ligating band dispenser with an inner tube that moves with respect to an outer tube to dispense a ligating band. This dispenser is oriented at right angles to the rigid endoscope and includes a structure for moving the inner tube of the dispenser in this configuration.

U.S. Pat. No. 4,735,194 to Stiegmann discloses a flexible endoscope ligating instrument in which a flexible endoscope structure includes a biopsy channel and a suction channel extending between the proximal and distal ends. A dispenser, like the dispenser structure shown in the Van Hoorn and Goltner patents, includes an inner tube that moves axially with respect to an outer tube at the distal end of the instrument. The outer tube connects to the distal end of the endoscope. An operating mechanism in the form of a pull wire with a weighted handle maintains tension on the inner tube so it does not displace axially outward while the instrument is being positioned. For some applications it is suggested that the endoscope structure be inserted through an overtube to prevent premature dispensing. Suction can be applied to draw tissue into a central aperture of the dispenser. Then a surgeon pulls the handle and retracts the inner tube axially past the distal end of the outer tube to force the ligating band off the instrument onto the tissue.

Each of the foregoing instruments dispenses a single ligating band or a single set of ligating bands at a single location. None of the patents suggests dispensing ligating bands at discrete locations The Van Hoorn patent does disclose the possibility of depositing plural ligating bands However, Van Hoorn seems only to suggest dispensing plural ligating bands at a single site in a single operation The apparatus disclosed in the Van Hoorn, Göltner or Stiegmann patents apparently would have to rely on a surgeon's sense of touch in order to displace the inner tube by an incremental distance corresponding to the thickness of a stretched ligating band to deposit a plurality of bands at different sites. That would be very difficult to accomplish.

Indeed, when it is desired to deposit ligating bands at different sites, the common practice is to withdraw the entire instrument from the patient and load a new ligating band onto the inner tube Loading ligating bands on an instrument requires special tools and can be time consuming particularly if the special tooling must be retrieved to install each ligating band individually while the instrument is withdrawn. Each of these instruments requires some structure, such as special stoppers or overtubes, for preventing the premature dispensing of the ligating band Consequently, none of these instruments is readily adapted for dispensing ligating bands at different sites without withdrawing the instrument after each individual site is ligated.

SUMMARY

Therefore it is an object of this invention to provide an instrument that can dispense plural ligating bands in sequence at discrete sites.

Another object of this invention is to provide a ligating instrument that can deposit plural ligating bands in sequence without requiring the instrument to be removed from a patient after each ligation.

Still another object of this invention is to provide a ligating band dispenser for attachment to diverse introducer structures including rigid and flexible endoscopes for ligating tissue.

Still another object of this invention is to provide a dispenser for attachment to a ligating instrument that dispenses plural ligating bands at different locations, that is reliable and easy to use and that inherently prevents any premature dispensing of the ligating band during instrument positioning.

Yet still another object of this invention is to provide an improved method for applying multiple ligating bands at discrete sites without having to withdraw a ligating instrument after each ligation.

In accordance with one embodiment of this invention, a ligating band dispenser located at the distal end of an elongated introducer responds to manipulation of an operating structure at the proximal end of the introducer. The dispenser comprises first and second coaxially located, interfitted segments that support ligating bands at a plurality of axially spaced positions thereon. Each segment includes a spaced ligating band engagement structure for engaging portions of each ligating band or set of bands. One of the segments connects to the operating structure for being moved between first and second positions relative to the other of the segments. This motion dispenses one of the ligating bands from the distal end of the ligating instrument and moves the remaining ligating bands distally with respect to the dispensing means thereby to position a successive ligating band for being dispensed at a different site.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
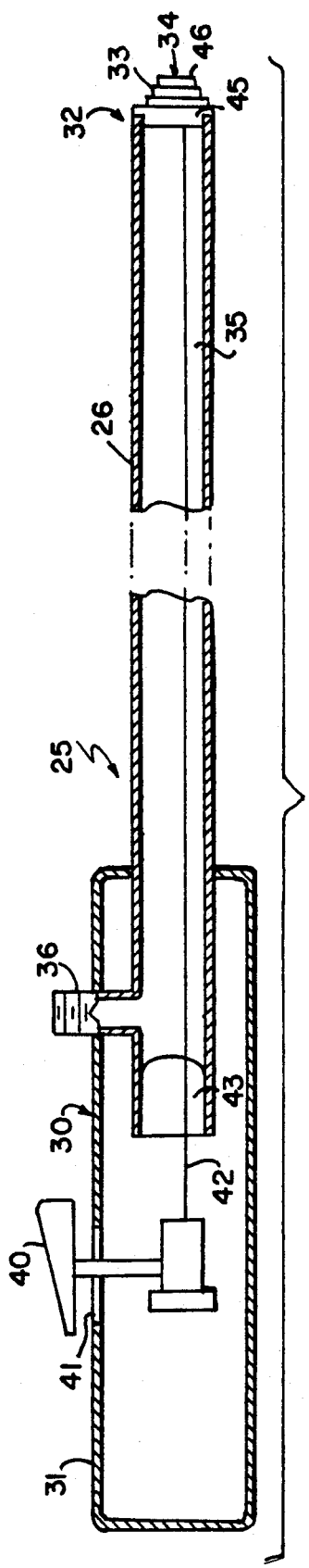
FIG. 1 depicts one embodiment of a ligating instrument constructed in accordance with this invention.

FIG. 1 depicts, in schematic form, one embodiment of a ligating instrument 25 that dispenses elastic ligating bands during a succession of operations. The ligating instrument includes an introducer in the form of an elongated, rigid tubular housing 26. A proximal end 30 of the tubular housing 26 connects to a handle 31 while the distal end 32 connects to a dispenser 33. The dispenser 33 is formed in a hollow tubular form to provide a central passage 34 that communicates with a central passage 35 through the tubular housing 26. A vacuum port 36 exits the tubular housing 26 at a proximal end 30 thereof through an aperture in the handle 31.

The handle 31 carries a trigger 40 that can be displaced axially in a slot 41. The trigger 40 attaches to a pull wire 42 that passes through a proximal seal 43 located at the proximal end 30 of the tubular housing 26 and connects to the dispenser 33. Diverse implementations of such a trigger and pull-wire operating structure can be incorporated in ligating instruments. The specifically disclosed embodiment is merely representative of such diverse implementations.

The proximal seal 43 allows vacuum to be applied through the vacuum port 36 and the central passages 34 and 35 while allowing reciprocal motion of the pull wire 42. With the proximal seal 43 in place, vacuum applied to the vacuum port 36 draws tissue into the central passage 34 for ligation. The trigger 40 and pull wire 42 constitute an operating structure that enables a surgeon to operate the dispenser 33, at the distal end 32, of the instrument 25 from the proximal end 30.

Figure 2:
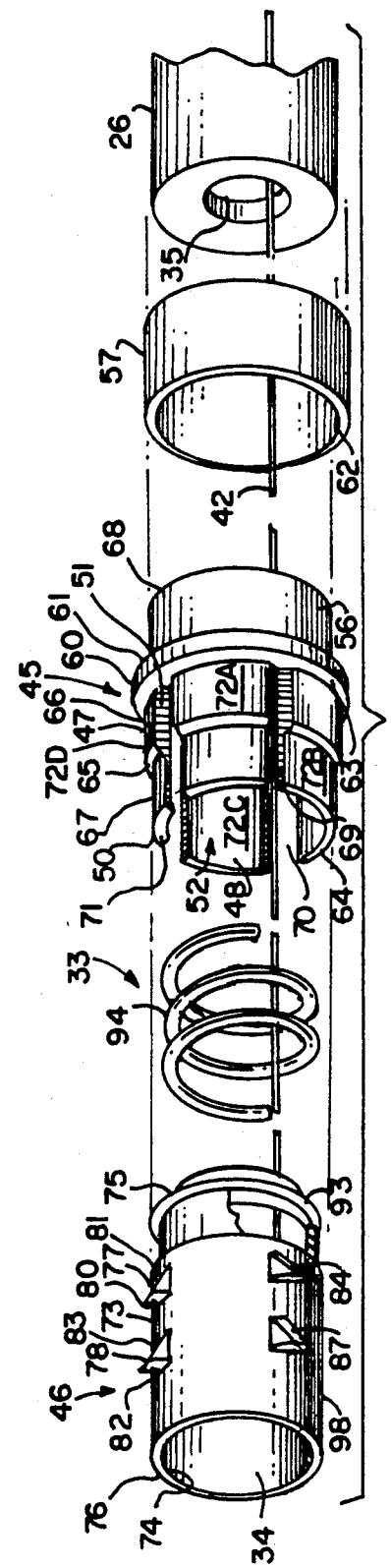
FIG. 2 is a perspective view of one embodiment of a ligating instrument dispenser constructed in accordance with this invention.

Referring to FIGS. 1 and 2, the dispenser 33 includes a housing segment 45 that attaches to the tubular housing 26. A piston segment 46 reciprocates with respect to the housing segment 45 between first and second positions under the control of the pull wire 42 or other structure.

Figure 3:
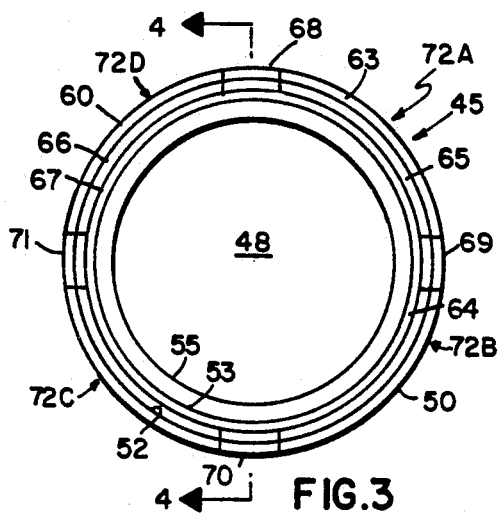
FIGS. 3 and 4 are views of a housing segment for use in the dispenser of FIG. 2 with FIG. 4 being a section taken along lines 4—4 in FIG. 3.
Figure 4:
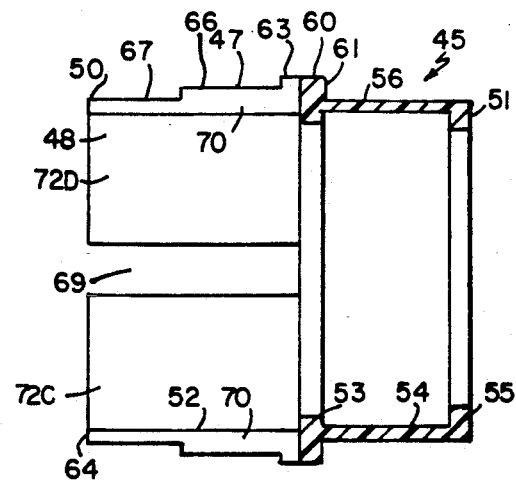

As shown in FIGS. 2 through 4, the housing segment 45 is formed as a generally tubular structure 47 with a central passage 48 between a distal housing end 50 and a proximal housing end 51. The tubular structure 47 has a first inner cylindrical surface 52 extending from the distal end 50 to an intermediately located circumferential central bead 53. A second inner cylindrical surface 54 shown in FIG. 4 extends from the central bead 53 to an annular, inturned, radially extending lip 55 at the proximal end 51.

Figure 7:
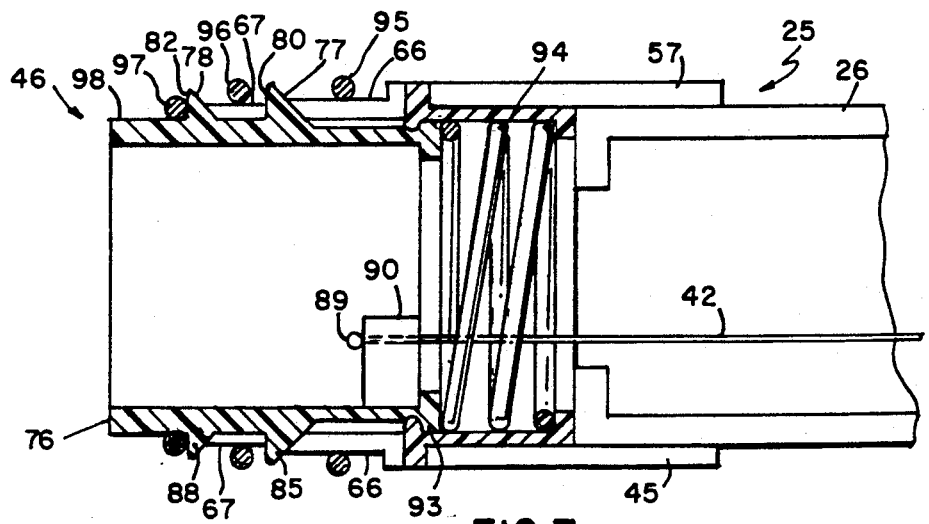
FIGS. 7 through 9 depict the assembly of the housing and piston segments of FIGS. 3 through 6 at different orientations.

In this particular embodiment an outer cylindrical surface 56, that is coextensive with the inner cylindrical surface 54 and the annular lip 55, provides an axially extending cylindrical hose means for connecting the housing segment 45 to the tubular housing 26 of FIGS. 1 and 2. As shown in FIG. 7, elastic tubing 57 overlies the outer cylindrical surface 56 and the distal end of the tubular housing 26 to affix the housing segment 45 to the tubular housing 26. A band 60 in FIGS. 3, 4 and 7 aligns axially with the central bead 53 to provide a shoulder 61 that receives an end 62 of the tube 57. The overlying tubing 57 can be replaced by any number of connecting structures that include threaded and mechanically or chemically bonded structures. The objective of any such structure is merely to affix the housing segment 45 to the end of the housing 26.

The portion of the housing segment 45 extending distally from the band 60 provides three axially spaced, radially extending shoulders including a shoulder 63 at the band 60, a shoulder 64 at the distal end 50 and an intermediate shoulder 65. These shoulders define limits of intermediate cylindrical surfaces 66 and 67. The cylindrical surface 67 is formed with a diameter that is less than the diameter of the cylindrical surface 66. As described particularly later, the resulting stepped cylindrical surfaces 66 and 67 are adapted for supporting ligating bands at axially spaced positions on the housing segment 45.

Still referring to FIGS. 2 through 4, each of the surfaces 66 and 67 has a generally cylindrical form divided into one of several arcuate fingers by axially extending slots 68, 69, 70 and 71. Finger 72A lies between slots 68 and 69; finger 72B, between slots 69 and 70; finger 72C, between slots 70 and 71; and finger 72D between slot 71 and 68.

Figure 5:
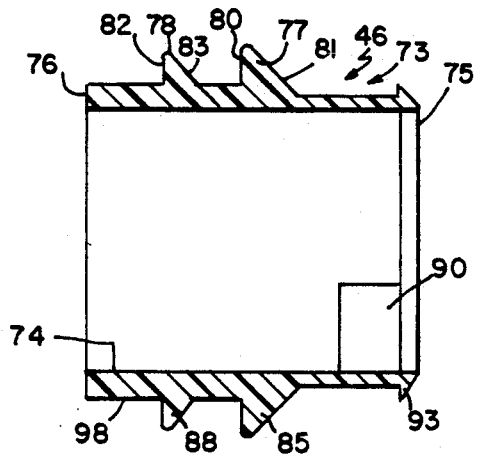
FIGS. 5 and 6 are views of a piston segment useful in the dispenser of FIG. 2 with FIG. 5 being a section taken along lines 5—5 in FIG. 6.
Figure 6:
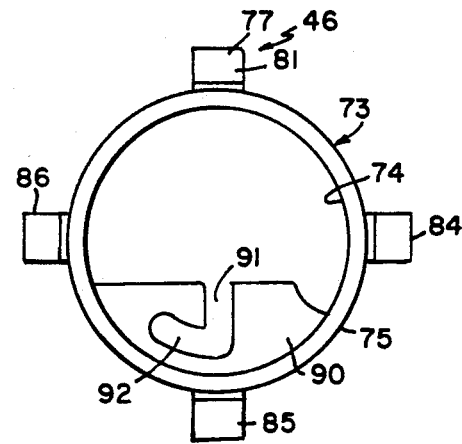

Now referring to FIGS. 2, 5 and 6, the piston segment 46 comprises a cylindrical base or tube 73 with an essentially inner cylindrical surface 74 between a proximal end 75 and a distal end 76. The tube 73 is formed with a plurality of circumferentially and axially spaced, radially extending fingers. Fingers 77 and 78, for example, are spaced axially with respect to each other and align with the slot 68. Each finger has a triangular cross section. For example, the finger 77 defines a distally facing, radial shoulder 80 and a proximally facing ramp surface 81. Likewise the finger 78 includes a distally facing shoulder 82 and a proximally facing ramp surface 83. The height of the finger 77 is greater than the height of the finger 78. As shown more particularly in FIG. 7, this height difference corresponds to the steps in the housing segment 45, so the shoulder 80 extends radially beyond the surface 66 of the housing segment 45 while the shoulder 82 extends radially beyond the surface 67.

The piston segment 46 additionally includes circumferentially spaced fingers 84, 85 and 86 aligned axially with the finger 77 and having the same relative form as the finger 77. Another set of circumferentially spaced fingers aligns axially with and have the same form as the finger 78. One such finger 87 is shown in FIG. 2; a finger 88 is shown in FIG. 5; another finger, not shown, aligns with the finger 86.

As shown in FIGS. 2 and 7, the pull wire 42 connects to the piston segment 46. In this specific embodiment the pull wire 42 terminates with a bead-like, enlarged head structure 89. As shown in FIGS. 5 and 6, the piston segment 46 includes a transverse member 90 adjacent the proximal end 75. A radially extending slot 91 leads from the interior of the tube 73 to an arcuate slot 92 located adjacent the tube 73. In practice the pull wire 42 passes through the slot 91 into the slot 92. Thereafter tension on the pull wire 42 causes the head 89 to engage a surface of the transverse member 90 adjacent the slot 92. The angle between the slots 91 and 92 minimizes any tendency of the pull wire 42 to disengage from the transverse member 90 while tension is applied.

As shown in FIGS. 2, 6 and 7, the proximal end 75 of the piston segment 46 terminates with frusto-conical lip 93 that tapers toward the proximal end 75. The lip 93 is configured to snap over the central bead 53 of the housing segment 45 thereby to limit distal motion of the piston segment 46 relative to the housing segment 45.

Referring again to FIGS. 2 and 7, the dispenser 33 is assembled by inserting a compression spring 94 into the housing segment 45 from the distal end 50 to be located intermediate the central bead 53 and the annular lip 55. In this position, the spring 94 is partially compressed. The piston segment 46 is inserted into the housing segment 45 until the lip 93 snaps over the central bead 53. Next the dispenser 33 can be mounted to a housing 26 as shown in FIG. 7 by a tube 57 or similar means. In this embodiment the pull wire 42 extends from the piston segment 46 through the spring 94 and the housing 26 to the proximal end thereof.

Prior to using the instrument 25, a plurality of elastic ligating bands are mounted on the dispenser 33 generally by using tooling that is similar to the tooling used with prior art ligating instruments. A first ligating band 95 is stretched onto the cylindrical surface 66; and a second ligating band 96, onto the surface 67. A third ligating band is stretched onto a distal end surface 98 of the piston 46.

In use the surgeon initially positions the distal end 76 of the piston segment 46 closely adjacent to the tissue to be ligated. If the ligating instrument 25 has a vacuum port, suction is used to draw the tissue into the instrument through the distal end 76.

Figure 8:
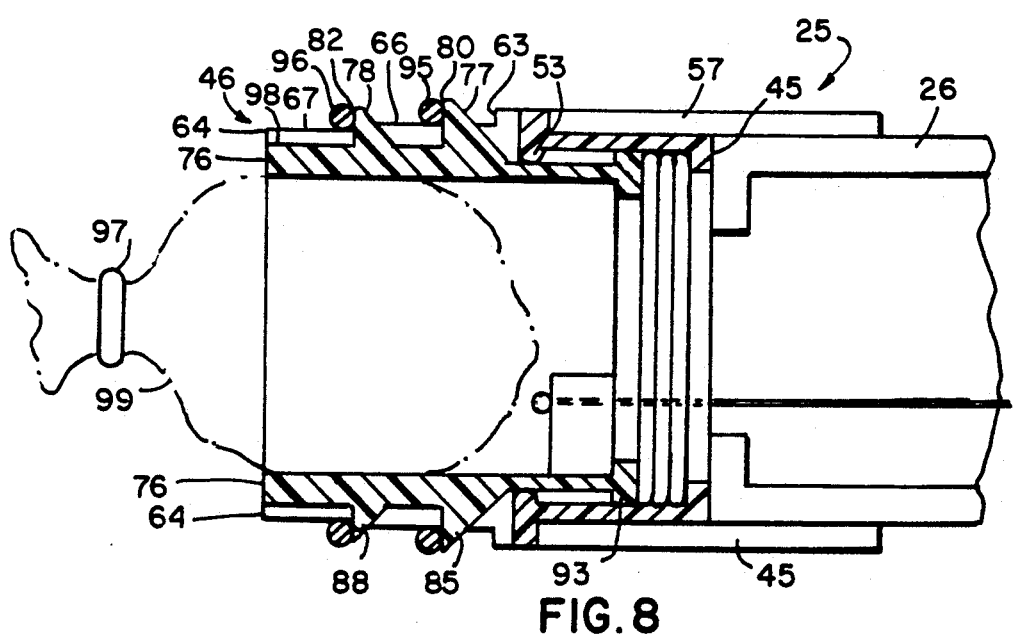

When the surgeon thereafter retracts the trigger 40 in FIG. 1, the pull wire 42 moves the piston segment 46 proximally with respect to the housing segment 45 from the position shown in FIG. 7 to the position shown in FIG. 8. This further compresses the spring 94 When the fingers, such as fingers 77 and 85, abut the shoulder 63, or some other stop engages, retraction terminates. During this retraction to a well defined end position, the shoulder 64 formed by the housing segment 45 at the distal end 50 thereof slides over the surface 98 of the piston segment 46 and engages the ligating band 97. Continued retraction of the piston segment 46 causes the ligating band 97 to move over the surface 98 until it reaches the distal end 76 and collapses from the surface 98 to ligate the tissue 99.

Simultaneously each of the fingers, such as fingers 77 and 78, 85 and 88, also retract. Initially the ramp surfaces of each finger will engage each correspondingly positioned ligating band. For example, during the operation depicted in FIGS. 7 and 8, the ramp surfaces of the fingers 77 and 85 initially engage the ligating band 95 while the fingers including fingers 78 and 88 engage the ligating band 96. As these fingers essentially make point contact with the ligating bands, the bands 95 and 96 expand locally and radially. However, the shoulders 63 and 65 prevent any proximal axial displacement of the bands 95 and 96. As the fingers pass the ligating bands, as shown particularly in FIG. 8, the bands drop to positions that are distally located with, respect to the fingers For example, the ligating band 96 lies against the shoulder 82 of the finger 78 while the ligating band 95 lies against the shoulder 80 of the finger 77. Consequently only one ligating band 97 is dispensed when the instrument 25 is positioned as shown in FIG. 8. The remaining ligating bands 95 and 96 remain on the instrument 25.

Figure 9:
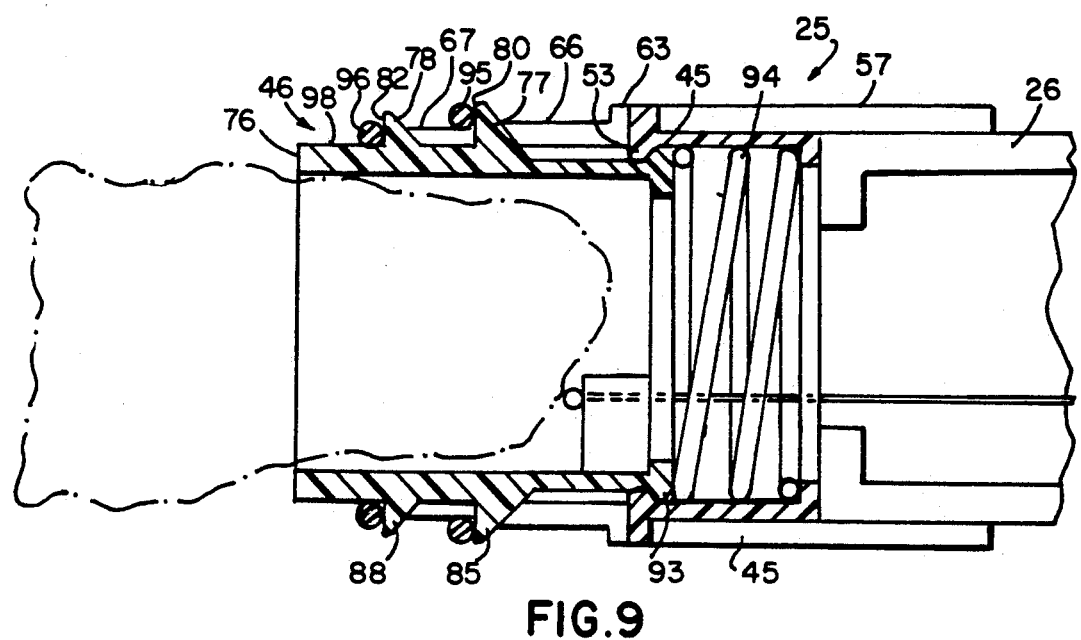

When the surgeon releases the trigger 40 in FIG. 1, the spring 94 drives the piston segment 46 distally until the lip 93 engages the central bead 53 as shown in FIGS. 8 and 9. During this motion, the various fingers, including fingers 77, 78, 85 and 88 advance the ligating bands 95 and 96 distally and axially. More specifically the circumferentially aligned fingers, including fingers 78 and 88, drive the ligating band 96 distally from the surface 67 onto the surface 98. The other aligned fingers, including fingers 77 and 85 drive the ligating band 95 from the surface 66 to the distal end surface 76 of the piston segment 46.

Now the surgeon can immediately position the distal end 76 of the instrument proximate another area for ligation and repeat the sequence. Consequently in this particular embodiment, it is possible for the surgeon to ligate three areas without removing the ligating instrument 25 from the patient. Each ligation merely requires the surgeon to position the instrument, to draw tissue into the instrument, to pull a trigger between two limited positions to dispense a single ligating band and release the trigger to prepare for a second sequence. There is no necessity for the surgeon to remove the instrument or to exercise sensitive and difficult control over the relative position of the piston 46 in order to provide this sequential dispensing operation.

These and other advantages are achieved by the coaxial configuration of the housing segment 45 and piston segment 46 as interfitted segments for supporting the ligating bands at the plurality of axially spaced positions, as on surfaces 66, 67 and 98. The fingers, such as fingers 77 and 78, engage the ligating bands, so the piston segment 46 can move between a first position as shown in FIG. 7 and a second position as shown in FIG. 8 and dispense one ligating band from the distal end of the ligating instrument 25. The subsequent return of the piston segment 46 with its fingers moves each of the remaining ligating bands distally and axially with respect to the ligating instrument 25 to prepare for a next operation. Moreover, the spring 94 biases the piston segment 46 distally with sufficient force to prevent premature dispensing of a ligating band from the surface 98.

Figure 10:
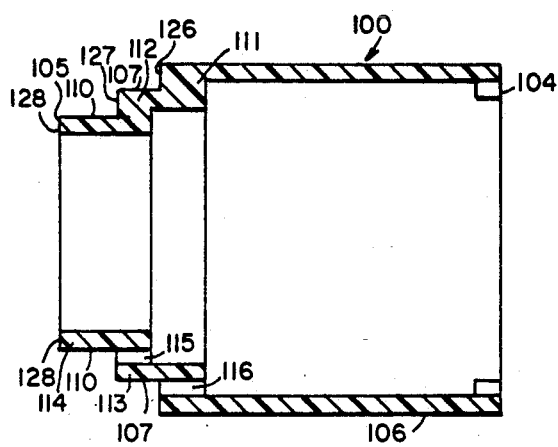
FIG. 10 is a view of a housing segment of another dispenser constructed in accordance with this invention.
Figure 11:
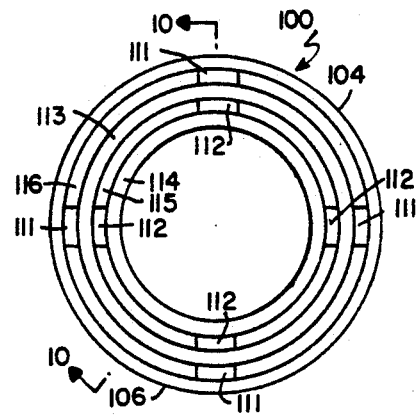
FIG. 11 is an end view taken from the left side of FIG. 10.
Figure 12:
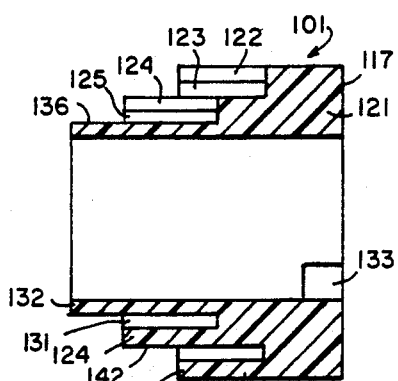
FIG. 12 is a view of a piston useful with the housing shown in FIGS. 10 and 11.
Figure 13:
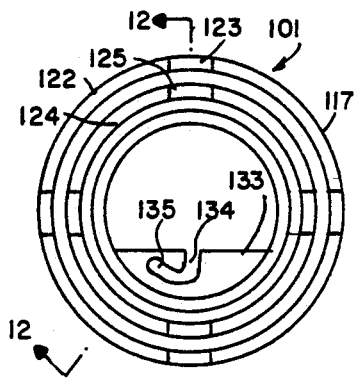
FIG. 13 is an end view taken from the left side of FIG. 12.
Figure 14:
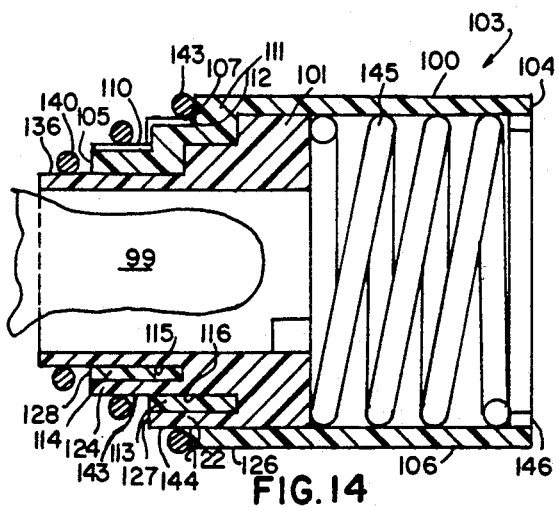
FIGS. 14 and 15 are views of an assembly of the housing and piston embodiment shown in FIGS. 10 through 13 at different orientations.
Figure 15:
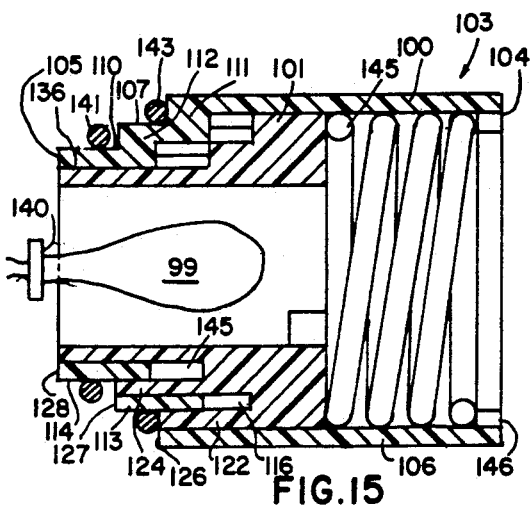

FIGS. 10 through 15 depict another embodiment of a dispenser for providing a similar operation. This dispenser is also adapted for use with a ligating instrument 25 such as shown in FIG. 1 or other introducers that may include a rigid or flexible endoscopic device. In this particular embodiment, a housing segment 100, as shown in FIGS. 10 and 11, and a piston segment 101, as shown in FIGS. 12 and 13, form a dispenser 103 as shown in FIGS. 14 and 15.

Referring to FIGS. 10 and 11, the housing segment 100 extends between a proximal end 104 and a distal end 105 and has a main cylindrical body portion 106. As the housing segment 100 extends toward the distal end 105, it forms a series of stepped surfaces of decreasing radius that include an intermediate surface 107 and a distally located surface 110.

The housing segment 100 is integrally molded with a plurality of connecting portions 111 and 112 equiangularly spaced about the housing segment 100. In the specific embodiment shown in FIGS. 10 and 11, the connecting portions 111 and 112 are spaced by 90°; however, other angles can also be used. The connecting portions 111 and 112 support the remaining portions of the housing segment 100 that form annular ring-like structures 113 and 114 intermediate the connecting portions 111 and 112. The annular structures 113 and 114 are radially displaced with respect to other portions of the housing segment 100 to define a plurality of arcuate openings 115 and 116 intermediate each of the connecting portions 112 and 111 respectively. The openings 115 and 116 receive interfitting portions of the piston segment 101.

FIGS. 12 and 13 disclose the piston segment 101 that extends between a proximal end 117 and a distal end 120 and has a solid ring structure 121 at the proximal end that constitutes a cylindrical body portion. A series of arcuate segments extend at different radii from this ring 121. For example, outer arcuate segments 122 are disposed at a maximum radius. These segments 122 are interrupted by axially extending slots 123. The diameter of the openings 116 determines the diameter of the arcuate segments 122 in the housing segment 100 shown in FIG. 10. Another set of arcuate segments 124 are formed at smaller radius and are interrupted by slots 125. The diameter of the arcuate openings 115 determine the diameter of the arcuate segments 124.

Referring again to FIGS. 10 and 11, the connecting portions 11 defines a first shoulder 126. The structures 113 terminate with second shoulder 127 that are axially and distally displaced with respect to the shoulder 126. The structures 114 terminate in shoulders 128 at the distal end 105. Thus, the shoulders 126, 127 and 128 and the surfaces 107 and 110 form an axially displaced, distally extending stepped surface. Similarly, the segments 122 in the piston segment 101, as shown in FIG. 12, form a shoulder 130. The distal end of the segment 124 forms a shoulder 131 and at the distal end 120 there is a shoulder 132.

The piston segment 101 additionally includes a transverse structure 133 that includes a radial slot 134 and an arcuate slot 135 for capturing a distal end of a pull wire. This structure 133 is analogous to the transverse structure 90 and slots 91 and 92 shown in FIG. 6.

During assembly, the piston segment 101 of FIGS. 12 and 13 mounts, in an interfitting fashion, in the housing segment 100 shown in FIGS. 10 and 11 from the proximal end 104. As shown in FIGS. 14 and 15, each of the arcuate segments 122 and 124 interfit with the arcuate openings 116 and 115. In a fully extended position as shown in FIG. 14, a distal end surface 136 on the piston segment 101 extends beyond the distal end 105 of the housing segment 100. This surface 136 receives a ligating band 140. A second ligating band 141 lies on a surface 142 intermediate the shoulders 130 and 131. A third ligating band 143 lies on a surface 144 that extends proximally from the shoulder 130.

When a ligating instrument, attached to the dispenser 103 shown in FIGS. 14 and 15 is properly positioned, suction can be applied to draw the tissue 99 into the dispenser 103 along its axis. Then the surgeon retracts the piston segment 101 proximally with respect to the housing segment 100. That motion compresses a spring 145. The shoulders 126, 127 and 128 engage the ligating bands 143, 141 and 140, respectively to hold them in a fixed position relative to the housing segment 100 during this motion. When the piston segment 101 reaches its fully retracted position, as shown in FIG. 15, the ligating band 140 is pushed off the surface 136 to ligate the tissue 99. The shoulder 127 transfers the second ligating band 141 from the surface 142 to the surface 136. Likewise the shoulder 126 transfers the ligating band 143 from the surface 144 to the surface 142.

When the surgeon releases the trigger, the spring 145 advances the piston segment 101 distally back to the position shown in FIG. 14 except that the ligating bands 141 and 143 now lie where the ligating bands 140 and 141 were previously. The ligating instrument is then ready to dispense the ligating band 141 at some other site.

FIGS. 14 and 15 disclose a collar 146 that could be ultrasonically welded to the proximal end 104 of housing segment 100 after assembly. This collar 146 would capture the spring 145 and the piston segment 101 the housing segment 100. Other structures could be substituted. For example the distal end of an introducer, such as tubular housing 26 in FIG. 1, could abut the proximal end 104 of the housing segment 100 to confine the spring 145. Other structures could accommodate other alternatives for the introducer such as those including endoscopic structures.

Figure 16:
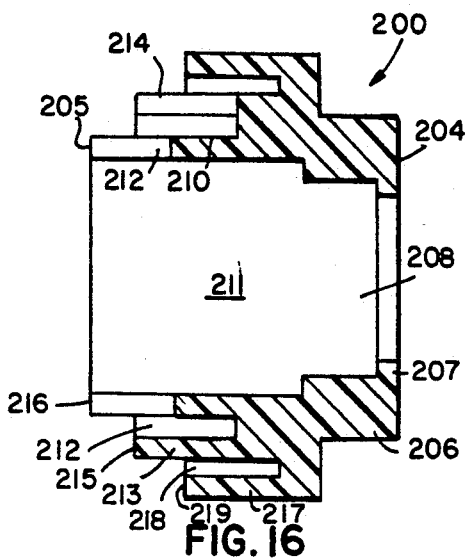
FIG. 16 is a view of a housing segment for another dispenser constructed in accordance with this invention.
Figure 17:
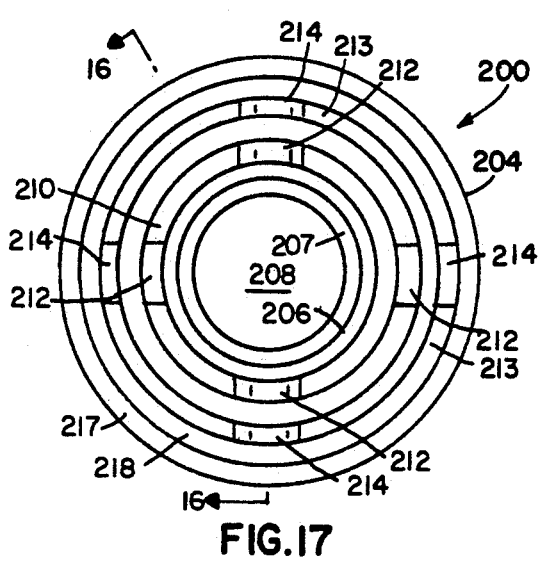
FIG. 17 is an end view taken from the left side of FIG 16.
Figure 18:
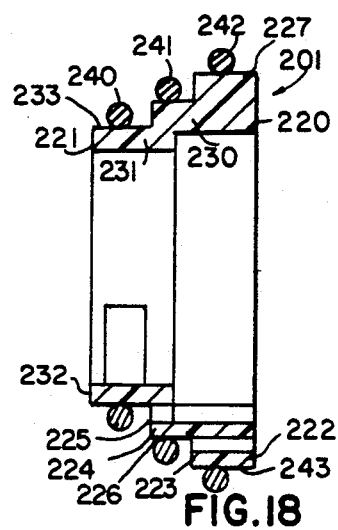
FIG. 18 is a view of a piston useful with the housing shown in FIGS. 16 and 17.
Figure 19:
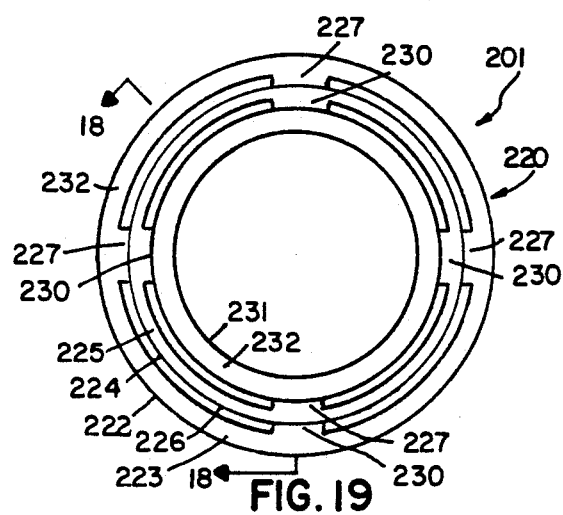
FIG. 19 is an end view taken from the left side of FIG. 18.
Figure 20:
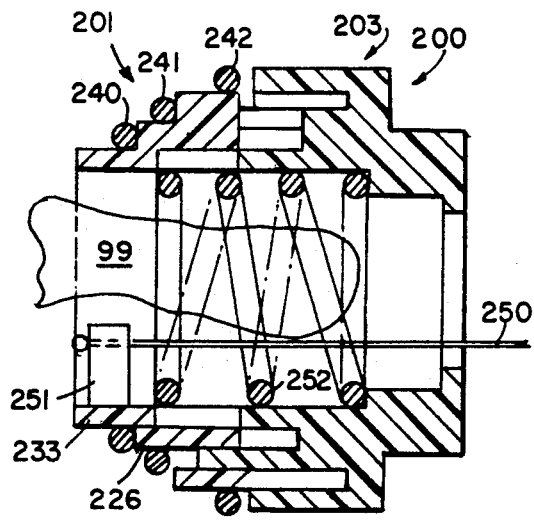
FIGS. 20 and 21 are views of an assembly of the housing and piston embodiments shown in FIGS. 16 through 19 at different orientations.
Figure 21:
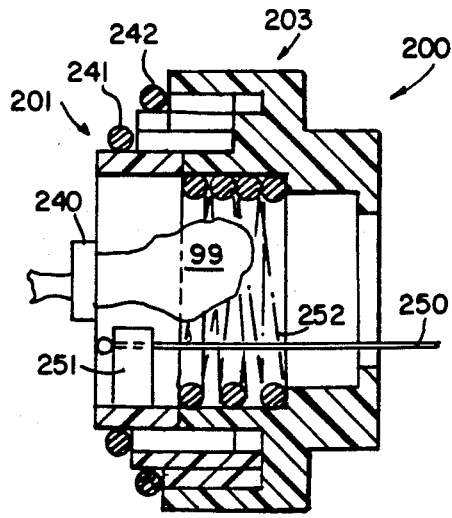

FIGS. 16 through 21 disclose another embodiment of a dispenser that includes a housing 200 shown in FIGS. 16 and 17 and a piston 201 shown in FIGS. 18 and 19 that are assembled into a dispenser 203 shown in FIGS. 20 and 21. The housing 200 extends from a proximal end 204 to a distal end 205. A ring-like body structure 206 at the distal end 205 has an inturned lip 207 and defines an internal chamber 208 of a given radius. A first series of axially extending fingers 210 extend from the structure 206 and form a second chamber 211 that has a larger radius than the chamber 208.

Equiangularly spaced axially extending slots 212, spaced at 90° in this particular embodiment, define four arcuate fingers 210 that axially extend from the ring 206 to the distal end 205. The ring 206 also supports another set of axially extending fingers 213 separated by equiangularly spaced slots 214. The fingers 213 terminate with distal end shoulders 215 that are proximally and axially spaced from shoulders 216 formed by the fingers 210. The fingers 213 lie on a radius that is greater than the radius that the fingers 210 define. The ring 206 also supports an arcuate ring 217 that is radially outwardly spaced from the fingers 213 and forms a channel 218. The ring 217 terminates with a shoulder 219.

The piston segment 201 shown in FIGS. 18 and 19 extends between a proximal end 220 and a distal end 221. A ring structure 222 at the proximal end has a diameter that corresponds to the nominal diameter of the channel slot 218 between the fingers 213 and 217 of the housing 200 in FIGS. 16 and 17. The ring structure 222 in FIGS. 18 and 19 terminates in a distal shoulder 223. A second ring structure 224, radially inwardly spaced from the ring structure 222, terminates distally in a shoulder 225. The shoulder 225 is axially offset in a distal direction respect to the shoulder 223 thereby to define an exterior cylindrical surface 226 intermediate the shoulder 223 and 225. Equiangularly spaced extensions 227 align with the slots 214 in FIGS. 16 and 17 and interconnect the ring structures 222 and 224. Other equiangularly spaced extensions 230 align with slots 212 and interconnect the ring 224 structure with an inwardly radially spaced ring structure 231. The ring structure 231 terminates at the distal end 221 with a shoulder 232 and that forms another exterior cylindrical surface 233 between the shoulders 225 and 232.

The piston segment 201 shown in FIGS. 18 and 19 can be used as a replaceable structure that is preloaded with ligating bands, such as ligating bands 240, 241 and 242. As shown in FIG. 18, the surfaces 233, 226 and a surface 243 support these ligating bands.

The piston segment 201 can be attached to the distal end 205 of the housing segment 200 shown in FIGS. 20 and 21. A pull wire 250, analogous to the pull wire 42 in FIG. 1, connects to a transverse attachment structure 251 formed inside the piston segment 201. A modification to the trigger could allow the extension of the trigger and the pull wire 250 by means of appropriate interlocking structure to a loading position to accommodate a replaceable piston segment 201. Such a structure would enable the pull wire 250 to extend for a distance sufficient to allow its ready connection to a transverse structure 251. After attachment, the trigger and pull wire 250 would return to a normal extended position as shown in FIG. 20. In this position a compressible spring 252, captured in the chamber 208 and extending distally to engage the transverse structure 251, would bias the piston segment 201 distally with respect to the housing segment 200.

After loading a piston segment 201 and positioning the instrument as shown in FIG. 20, the proximal end 220 of the piston segment 201 would align axially with the end of the ring 217. The combined forces produced by the spring 252 and the pull wire 250 would hold the piston segment 201 in the position shown in FIG. 20. However, the connecting structures 228 and 230 of the piston segment 201 also would align with the slots 214 and 212 of the housing segment 200 thereby to allow the piston segment 201 to move proximally under control of the pull wire 250.

A surgeon would position the ligating instrument containing the dispenser 203 at tissue 99 as shown in FIG. 20 and use vacuum or mechanical means to draw the tissue 99 into the dispenser 203. When the surgeon pulls the trigger, the pull wire 250 moves the piston segment 201 proximally to the position shown in FIG. 21. The shoulders 216, 215 and 219 due to their axial offsets, engage the ligating bands 240, 241 and 242 through the slots defined in the piston segment and displace the ligating bands axially with respect to the piston segment 201. At the retracted position shown in FIG. 21, each of these shoulders displaces the ligating bands 240 through 242 beyond the shoulders 232, 225 and 223 respectively. Consequently the ligating band 240 is dispensed to ligate the tissue 99. The ligating band 241 moves to the segment 210 while the ligating band 242 moves to the segment 213.

When the surgeon releases the trigger, the spring drives the piston segment 201 back to the position shown in FIG. 20. During this movement, the ligating band 241 rides on the surface 233 and advances axially and distally relative to the housing segment 200 while the ligating band 242 rides on the surface 226.

Each of the foregoing three embodiments shown in FIGS. 1 through 9, in FIGS. 10 through 15 and in FIGS. 16 through 21 discloses a ligating band dispenser for a ligating instrument. In each the dispenser can dispense a single ligating band at a given location. It will be apparent, however, multiple bands could be located at each axial position in any of the embodiments. In each of these embodiments a surgeon performs multiple ligating operations at different locations without having to withdraw the ligating instrument after each ligating band is dispensed.

Although this structure has been shown with respect to a particular ligating instrument, it will be apparent that a dispenser constructed in accordance with any of the disclosed embodiments is readily adapted for connection with introducers that can incorporate a wide variety of structures including those based upon rigid or flexible endoscopic structures. It will also be apparent that this dispenser is reliable, readily producible and structurally sound. The use of a compression spring prevents premature dispensing of the ligating bands so that the requirement for the use of over tubes or separate stoppers is not required with ligating instruments incorporating this invention.

Other structures for providing the reciprocal, definite motion of the piston member could be substituted for the spring and trigger operating mechanism. Other arrangements for holding the spring could be substituted to allow the dispenser to have a minimal length. This is particularly important when the dispenser attaches to an endoscopic device so that the dispenser does not unduly limit the field of view.

In use the ligating instrument is simple to use because it is merely necessary for the surgeon to position the ligating instrument and then move a trigger from one stop to another. There is no need for the surgeon to sense the amount of travel required for depositing a single ligating band or a single set of ligating bands.

While this invention has been disclosed in terms of three particular embodiments and certain modifications, it will be apparent that many other modifications can be made to the specifically disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. In a ligating instrument for dispensing a plurality of ligature means during a succession of operations wherein said ligating instrument includes elongated tubular introducer means extending between proximal and distal positions for attachment to ligature dispensing means and operating means at said distal and proximal positions, respectively, the improvement wherein said dispensing means comprises first and second coaxially located, interfitted segment means for supporting the plurality of ligature means at a plurality of axially spaced positions thereon, each of said segment means including spaced ligature engagement means for engaging portions of each of the ligature means and one of said segment means being connected to said operating means for being moved between first and second positions relative to the other of said segment means thereby to dispense one of said ligature means from the distal end of said ligating instrument and to move each of the remaining ligature means distally and incrementally with respect to said dispensing means.

2. A ligating instrument as recited in claim 1 wherein said first segment means is affixed to the introducer means and surrounds said second segment means and said second segment means connects to said operating means to move axially with respect to said first segment means.

3. A ligating instrument as recited in claim 2 wherein said first segment means comprises a plurality of axially displaced, cylindrical sections of decreasing radii, each said cylindrical section being adapted for supporting a ligature means.

4. A ligating instrument as recited in claim 3 wherein said second segment means is adapted for carrying a ligature means at its distal end.

5. A ligating instrument as recited in claim 4 wherein the instrument dispenses a predetermined plurality of ligature means and wherein said first and second segment means define, collectively, a plurality of radial surfaces equal to the predetermined plurality for engaging each ligature means during the axial displacement thereof.

6. A ligating instrument as recited in claim 5 wherein first segment means comprises an axially extending, cylindrical base and a plurality of circumferentially spaced, axially extending arcuate fingers supported by said base.

7. A ligating instrument as recited in claim 6 wherein said second segment means includes a cylindrical base having circumferentially and axially spaced fingers extending radially therefrom for extending outwardly between said arcuate fingers.

8. A ligating instrument as recited in claim 7 wherein said first and second segment means include detent means for capturing a proximal end of said second segment means in said first segment means thereby to limit axial displacement of said second segment means with respect to said first segment means.

9. A ligating instrument as recited in claim 8 additionally comprising spring means intermediate said first and second segment means thereby to bias said second segment distally with respect to said first segment means.

10. A ligating instrument as recited in claim 4 wherein the instrument dispenses a predetermined plurality of ligature means, wherein said second segment means includes a plurality of surfaces for supporting the ligature means and said first segment includes a plurality of radial surfaces for engaging each ligature means during axial displacement and wherein each of the pluralities of surfaces is equal to the predetermined plurality.

11. A ligating instrument as recited in claim 10 additionally comprising spring means intermediate said first and second segment means thereby to bias said second segment distally with respect to said first segment means.

12. A ligating instrument as recited in claim 11 wherein said first segment includes tubular housing means having radially spaced, axially extending annular structures terminating in shoulder portions for engaging each of the ligature means supported on said second segment.

13. A ligating instrument as recited in claim 12 wherein said second segment means includes piston means connected to the operating means for axial motion relative to said tubular housing means, said piston means including a plurality of arcuate segments aligned radially with said radially spaced annular structures on said tubular housing means whereby during proximal displacement of said piston means, said shoulder portions of said tubular housing means axially and distally displace the ligature means on said piston means.

14. A ligating instrument as recited in claim 13 wherein tubular housing includes an inner cylindrical surface extending from the proximal end thereof and said piston means includes a cylindrical body portion for engaging said inner cylindrical surface.

15. A ligating instrument as recited in claim 13 wherein said piston means includes a plurality of inner cylindrical surfaces and said tubular housing includes a plurality of exterior cylindrical surfaces for supporting said piston means whereby said piston means is readily detached from said tubular housing means.

16. A ligating instrument for positioning a plurality of ligating bands at a plurality of lesions comprising:
  A. ligating instrument introducer means for communicating between proximal and distal ends of said ligating instrument,
  B. operating means at the proximal end of said ligating instrument connected to said ligating instrument introducer means for controlling the dispensing of ligating bands, and
  C. dispensing means at the distal end of said ligating instrument introducer means for dispensing the ligating bands in sequence at discrete locations, said dispensing means including an interfitted tubular dispenser housing means and piston means for collectively supporting a plurality of axially spaced ligating bands thereon, each of said dispenser housing means and piston means having spaced ligating band engagement means for engaging portions of each of the ligating bands, said piston means being connected to said operating means for movement between proximal and distal positions wherein movement of said piston means proximally with respect to said dispenser housing means dispenses one of the ligating bands from the distal end of said ligating instrument and subsequent movement of said piston means distally transfers each of the remaining ligating bands distally with respect to said dispensing means.

17. A ligating instrument as recited in claim 16 wherein said dispensing means additionally includes spring means intermediate said dispenser housing means and said piston means for biasing said piston means distally with respect to said dispenser housing means.

18. A ligating instrument as recited in claim 17 comprising handle means at the proximal end of said lighting instrument introducer means and said operating means includes trigger means mounted to said handle means for reciprocal motion and interconnecting means attached between said trigger means and said piston means whereby proximal motion of said trigger means produces proximal motion of said piston means.

19. A ligating instrument as recited in claim 18 wherein said dispenser housing means attaches to said ligating instrument introducer means and comprises a plurality of axially displaced, cylindrical finger means of decreasing radii, each said finger means being adapted for supporting a ligating band.

20. A ligating instrument as recited in claim 19 wherein said piston means is adapted for carrying a ligating band at its distal end.

21. A ligating instrument as recited in claim 20 wherein the instrument dispenses a predetermined plurality of ligating bands and wherein said dispenser housing means and said piston means collectively define a plurality of radial surfaces equal to the predetermined plurality for engaging each ligating band during the axial displacement thereof.

22. A ligating instrument as recited in claim 21 wherein said piston means includes a cylindrical base having circumferentially and axially spaced fingers extending radially therefrom for extending outwardly between said finger means on said housing.

23. A ligating instrument as recited in claim 22 wherein said dispenser housing means and said piston means include detent means for capturing a proximal end of said piston means in said dispenser housing means thereby to limit axial displacement of said piston means with respect to said dispenser housing means.

24. A ligating instrument as recited in claim 18 wherein the ligating instrument dispenses a predetermined plurality of ligating bands wherein said piston means includes a plurality of surfaces for supporting the ligating bands and said dispenser housing means includes a plurality of radial surfaces for engaging each ligating band during axial displacement and wherein each of the plurality of surfaces is equal to the predetermined plurality.

25. A ligating instrument as recited in claim 24 wherein said dispenser housing means includes a cylindrical body portion and radially spaced, axially extending annular structures extending from said body portion and terminating in shoulder portions for engaging each of the ligating bands supported on said piston means.

26. A ligating instrument as recited in claim 25 wherein said piston means includes a plurality of arcuate segments aligned radially with said radially spaced annular structures on said dispenser housing means whereby during proximal displacement of said piston means, said shoulder portions of said dispenser housing means axially and distally displace the ligating bands axially and distally on said piston means.

27. A ligating instrument as recited in claim 26 wherein dispenser housing includes an inner cylindrical surface extending from the proximal end thereof and said piston means includes a cylindrical body portion for engaging said inner cylindrical surface.

28. A ligating instrument as recited in claim 26 wherein said piston means includes a plurality of inner cylindrical surfaces and said dispenser housing means includes a plurality of exterior cylindrical surfaces for supporting said piston means whereby said piston means is radially detached from said dispenser housing means.

29. A method for dispensing a plurality of ligating bands at a plurality of discrete locations including the steps of:
A. providing a ligating instrument having a hollow dispenser at the distal end thereof that carries the plurality of ligating bands at axially displaced positions thereon and that includes an interfitted housing and piston movable with respect to the housing, each of the housing and piston having engagement means for dispensing one ligating band from the distal end of the ligating instrument,
B. inserting the ligating instrument into a patient's body, and
C. ligating tissue at a plurality of locations within the patient's body by, for each location,
 i. locating the distal end of the ligating instrument proximate tissue to be ligated,
 ii. drawing the tissue to be ligated into the hollow dispenser thereby to position the distal end of the ligating instrument at the position for applying the ligating band,
 iii. retracting the piston relative to the housing thereby to dispense one of the plurality of ligating bands and ligate the tissue, and
 iv. moving the piston distally thereby to advance the piston whereby the engagement means move remaining ligating bands on the dispenser distally and axially, and
D. withdrawing the ligating instrument from the patient after the plurality of ligating bands have been dispensed.

* * * * *